(12) United States Patent
Awan et al.

(10) Patent No.: US 9,737,732 B2
(45) Date of Patent: Aug. 22, 2017

(54) MACHINE VISION SYSTEM

(71) Applicant: Elekta AB (publ), Stockholm (SE)

(72) Inventors: Shakil Ahmed Awan, Crawley (GB); Adrian Maxwell Smith, London (GB)

(73) Assignee: Elekta AB (publ), Stockholm (SE)

( * ) Notice: Subject to any disclaimer, the term of this patent is extended or adjusted under 35 U.S.C. 154(b) by 0 days.

(21) Appl. No.: 15/337,501

(22) Filed: Oct. 28, 2016

(65) Prior Publication Data

US 2017/0043185 A1    Feb. 16, 2017

Related U.S. Application Data

(63) Continuation of application No. 12/362,664, filed on Jan. 30, 2009, now abandoned.

(30) Foreign Application Priority Data

Feb. 1, 2008    (GB) .................................. 0801895.4

(51) Int. Cl.
*G01K 1/04*    (2006.01)
*A61N 5/10*    (2006.01)
(Continued)

(52) U.S. Cl.
CPC ......... *A61N 5/1049* (2013.01); *A61N 5/1042* (2013.01); *A61N 5/1045* (2013.01);
(Continued)

(58) Field of Classification Search
CPC ............. G21K 1/046; G21K 2201/067; A61N 5/1045; A61N 5/1036; A61B 6/08;
(Continued)

(56) References Cited

U.S. PATENT DOCUMENTS

| 7,148,974 B1 | 12/2006 | Schmitt et al. |
| 2004/0240621 A1 | 12/2004 | Noguchi |

(Continued)

FOREIGN PATENT DOCUMENTS

| EP | 0314231 A2 * | 3/1989 |
| EP | 0314231 A2 | 5/1989 |

(Continued)

OTHER PUBLICATIONS

Patent Abstract of Japan, Publication No. 03025820, published Feb. 4, 1991, Mitsubishi Electric Corp.

(Continued)

*Primary Examiner* — Hoon Song
(74) *Attorney, Agent, or Firm* — Westman, Champlin & Koehler, P.A.; Z. Peter Sawicki; Amanda M. Prose

(57) ABSTRACT

A fluorescing marker is used in order to mark (for example) a leaf of a multi-leaf collimator and/or the reference points within the field of view. The markers are illuminated with light tuned to cause the markers to fluoresce at a wavelength different to that of the illuminating light. The fluorescence is then detected by a camera. This method allows the image to be captured by the camera with increased contrast. Accordingly, the present invention provides a multi-leaf collimator for a radiotherapeutic apparatus, comprising at least one leaf having a fluorescent marker. The fluorescent marker will usually emit light of a wavelength longer than the incident light, allowing suitable filters to be provided in order to distinguish the light emitted by the markers. A suitable material for use in the fluorescent markers is ruby. The present invention also provides a radiotherapeutic apparatus comprising a multi-leaf collimator as defined above, and a camera arranged to view the fluorescent markers. A source of illumination for the fluorescent markers is ideally monochromatic, or nearly so. The camera can have a filter (Continued)

arranged to substantially prevent light of the wavelength emitted by the source of illumination from entering the camera, thereby improving the contrast of the image. The radiotherapeutic apparatus can also comprise a source of illumination that is optically co-located with a radiation source, to allow the radiation field that will be emitted to be checked visually by an operator. The co-located source is preferably substantially monochromatic, emitting substantially no light at the wavelength of the fluorescent markers. A filter can then be placed over an output of the radiotherapeutic apparatus, for blocking light of the wavelength of the fluorescent markers and thereby enhancing the contrast of the image that is taken of the fluorescent markers.

19 Claims, 2 Drawing Sheets

(51) Int. Cl.
G21K 1/04 (2006.01)
G06T 7/00 (2017.01)
H04N 5/225 (2006.01)
A61B 90/00 (2016.01)

(52) U.S. Cl.
CPC .............. *G06T 7/0012* (2013.01); *G21K 1/04* (2013.01); *G21K 1/046* (2013.01); *H04N 5/2256* (2013.01); *A61B 2090/3941* (2016.02); *A61N 5/1048* (2013.01); *A61N 2005/1059* (2013.01); *G06T 2207/10064* (2013.01); *G06T 2207/30204* (2013.01)

(58) Field of Classification Search
CPC ....... A61B 6/587; A61B 6/547; A61B 6/0492; A61B 6/06
See application file for complete search history.

(56) References Cited

U.S. PATENT DOCUMENTS

| 2005/0054456 A1 | 3/2005 | Gobush |
| 2005/0090875 A1 | 4/2005 | Palanker et al. |
| 2005/0159231 A1 | 7/2005 | Gobush |
| 2006/0173294 A1 | 8/2006 | Ein-Gal |

FOREIGN PATENT DOCUMENTS

| EP | 1467311 A1 | 10/2004 |
| EP | 1815883 A1 | 8/2007 |
| GB | 2403884 A1 | 1/2005 |
| WO | 03010567 A2 | 2/2003 |
| WO | 03077813 A1 | 9/2003 |

OTHER PUBLICATIONS

European Search Report of Application No. EP 09000841, Apr. 29, 2009.
UK Search Report of Application No. GB0801895.4, Apr. 23, 2008.

\* cited by examiner

MACHINE VISION SYSTEM

CROSS-REFERENCE TO RELATED APPLICATION

The present application is a continuation of and claims priority of U.S. patent application Ser. No. 12/362,664, filed Jan. 30, 2009, which claims priority of British patent application Serial No. 0801895.4, filed Feb. 1, 2008, the contents of which are hereby incorporated by reference in their entirety.

FIELD OF THE INVENTION

The present invention relates to a machine vision system. It provides a solution to problems that arise in machine vision applications in hostile or otherwise difficult environments, such as the interior of a radiotherapeutic apparatus.

BACKGROUND ART

Radiotherapeutic apparatus involves the production of a beam of ionising radiation, usually x-rays or a beam of electrons or other sub-atomic particles. This is directed towards a cancerous region of the patient, and adversely affects the tumour cells causing an alleviation of the patient's symptoms. Generally, it is preferred to delimit the radiation beam so that the dose is maximised in the tumour cells and minimised in healthy cells of the patient, as this improves the efficiency of treatment and reduces the side effects suffered by a patient. A variety of methods of doing so have evolved.

One principal component in delimiting the radiation dose is the so-called "multi-leaf collimator" (MLC). This is a collimator which consists of a large number of elongate thin leaves arranged side to side in an array. Each leaf is moveable longitudinally so that its tip can be extended into or withdrawn from the radiation field. The array of leaf tips can thus be positioned so as to define a variable edge to the collimator. All the leaves can be withdrawn to open the radiation field, or all the leaves can be extended so as to close it down. Alternatively, some leaves can be withdrawn and some extended so as to define any desired shape, within operational limits. A multi-leaf collimator usually consists of two banks of such arrays, each bank projecting into the radiation field from opposite sides of the collimator.

It will of course be necessary to monitor the current actual position of the leaves in order to provide feedback and allow their position to be adjusted accurately. To date, two main methodologies have been employed in order to do so, namely;

Optical vision position sensing

Traditional positional sensing, for example potentiometers, encoders etc

The approach to the problem of accurate leaf positional readout adopted to date by the applicant is outlined in FIG. 1. The solution is based on a vision system whereby a camera system "views" 84 different reflectors. 4 of these reflectors are reference markers, one in each corner of the viewable area, and 80 of these mark the individual position of each leaf of the two opposing banks of 40 leaves. The position of each leaf can therefore be calculated. The reflector is one having retro-reflective properties, i.e. light is reflected back along the same path as the incident light.

Thus, a camera 10 views the collimator leaves 12, 14, via a pair of tilt-adjustable mirrors 16, 18 which permit the camera to be located out of the radiation beam. A beam splitter 20 is placed in the optical path (between the two mirrors 16, 18 so that it is also out of the radiation beam) to allow a light projector 22 to illuminate the collimator leaves 12, 14 along the same optical path. A further mirror or mirrors 24 can be provided so as to locate the light projector (and/or other elements) in convenient locations.

Others tend to utilise traditional measurement methodologies. This involves measuring the position of each leaf by an individual sensor. A common design requirement is fault tolerance, or "single fault tolerance", which implies that in order to assure the correct position of a single leaf, a secondary or back-up sensor must be used. This therefore doubles the number of position sensors required.

Various problems exist with both approaches. Optical methodologies and other current machine vision solutions require a high uniformity of illumination, which leads to difficulty in the recognition of valid reflectors. The leaf reflector material has only a limited lifetime, due to dirt and surface damage. The reflector material must be mounted with a high degree of accuracy. Stray light and/or stray reflections from internal reflections and/or reflections off a treatment table top can confuse the system. Finally, the retro-reflective properties of the leaf markers require the light source and the camera position to be in an optically identical location, to very tight tolerances, otherwise the shape and apparent brightness of the marker changes.

Traditional position measurement methodologies also suffer from serious difficulties. In particular, a very large number of sensors is required—a minimum two sensors per leaf to provide one primary readback and one backup readback. The degree of accuracy required and the quantity of sensors used conspire to mean that the system as a whole has a generally low degree of reliability. Further, there are difficulties in packaging the required quantity of sensors in a sufficiently compact design, and the sensors suffer from potentially poor reliability due to the radiation damage that inevitably results from their field of use.

SUMMARY OF THE INVENTION

The invention involves the use of a fluorescing marker in order to mark a leaf and/or the reference points within the field of view. The markers are illuminated with light tuned to cause the markers to fluoresce at a wavelength different to that of the illuminating light. The fluorescence is then detected by a camera. This method allows the image to be captured by the camera with increased contrast.

A fluorescing marker is one that accepts incident light energy and emits light at a different wavelength (or frequency). This differs from simple reflection or retro-reflection, in which the reflected light is of substantially the same wavelength as that which was incident.

Accordingly, the present invention provides a multi-leaf collimator for a radiotherapeutic apparatus, comprising at least one leaf having a fluorescent marker.

It is naturally preferred that substantially all the leaves of the collimator have a fluorescent marker. However, it is not inconceivable that a mixed system could be provided.

The leaves will typically be mounted in a frame of some sort. It will usually be advantageous for the frame itself to have one or more fluorescent markers, preferably several so as to collectively indicate a maximum field of view of the collimator and provide a frame reference.

The fluorescent marker will usually emit light of a wavelength longer than the incident light, allowing suitable filters to be provided in order to distinguish the light emitted by the markers. A suitable material for use in the fluorescent markers is ruby. This can be in a spherical or a cylindrical shape, or another suitable shape. Several markers could of course be provided on a single leaf or leaves, ideally in different configurations so as to achieve greater accuracy and/or robustness of identification.

The present invention also provides a radiotherapeutic apparatus comprising a multi-leaf collimator as defined above, and a camera arranged to view the fluorescent markers. A source of illumination for the fluorescent markers will also be useful and is ideally monochromatic or nearly so. The camera can have a filter arranged to substantially prevent light of the wavelength emitted by the source of illumination from entering the camera, thereby improving the contrast of the image.

The radiotherapeutic apparatus can also comprise a source of illumination that is optically co-located with a radiation source, to allow the radiation field that is being emitted or will be emitted to be checked visually by an operator. The co-located source is preferably substantially monochromatic, emitting substantially no light at the wavelength of the fluorescent markers. A filter can then be placed over an output of the radiotherapeutic apparatus, for blocking light of the wavelength of the fluorescent markers and thereby enhancing the contrast of the image that is taken of the fluorescent markers.

BRIEF DESCRIPTION OF THE DRAWINGS

An embodiment of the present invention will now be described by way of example, with reference to the accompanying figures in which.

DETAILED DESCRIPTION OF THE EMBODIMENTS

The present invention will be described in relation to sensing the position of a large number of MLC leaves within a radiotherapeutic apparatus. As noted above, these leaves operate within a harsh environment in terms of the ionising radiation that is deliberately created within the radiotherapy head and into which they must project in order to carry out their function. This harshness presents difficulties in the provision of a machine vision solution to leaf monitoring that is stable and reliable in the long term. The solution adopted in relation to the MLC leaves is of course applicable in other situations, particularly (but not exclusively) environments that are harsh or which present difficulties in distinguishing illuminated markers.

Figure 1:
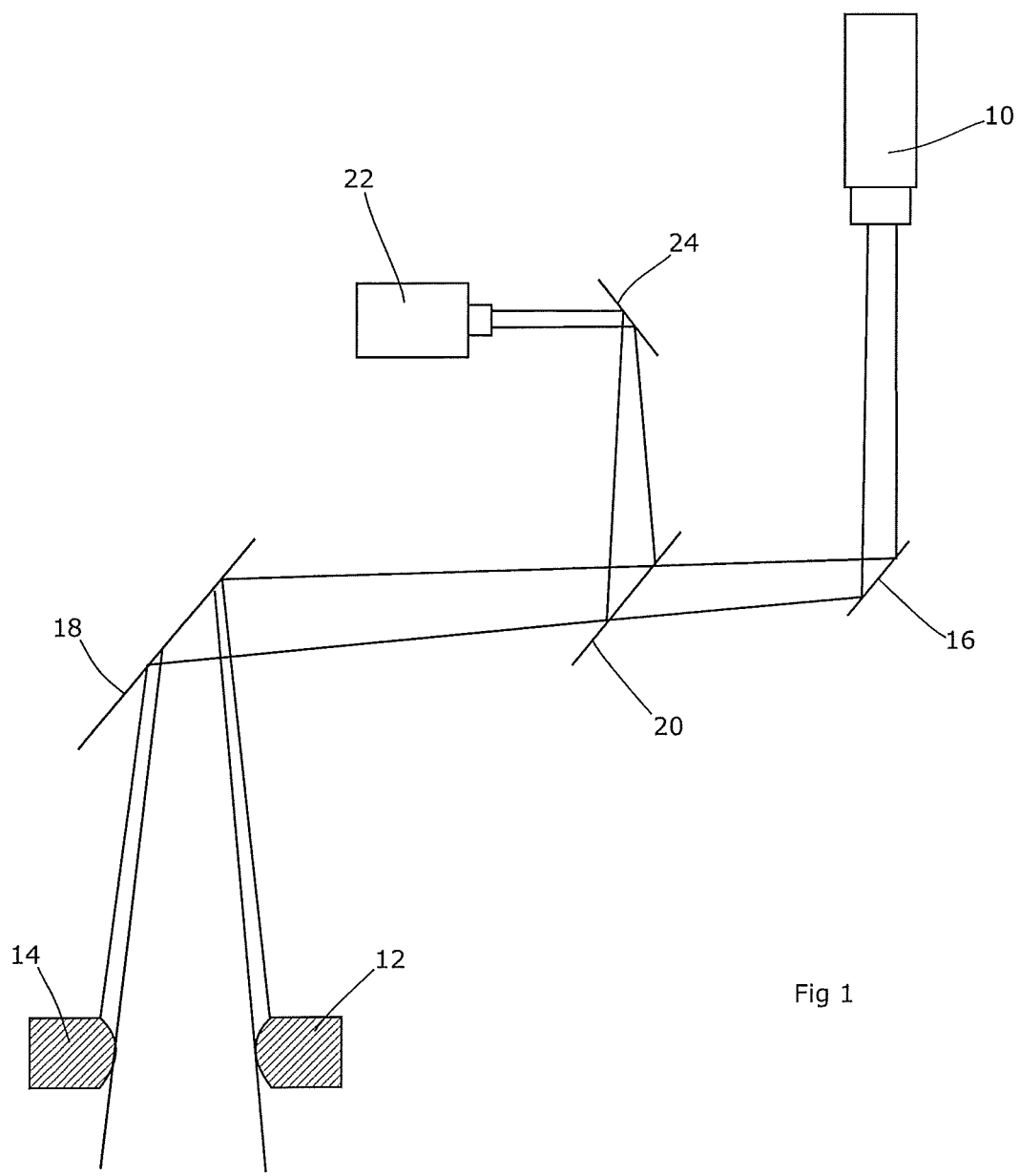
FIG. 1, described above, shows a known positional readout arrangement.
Figure 2:
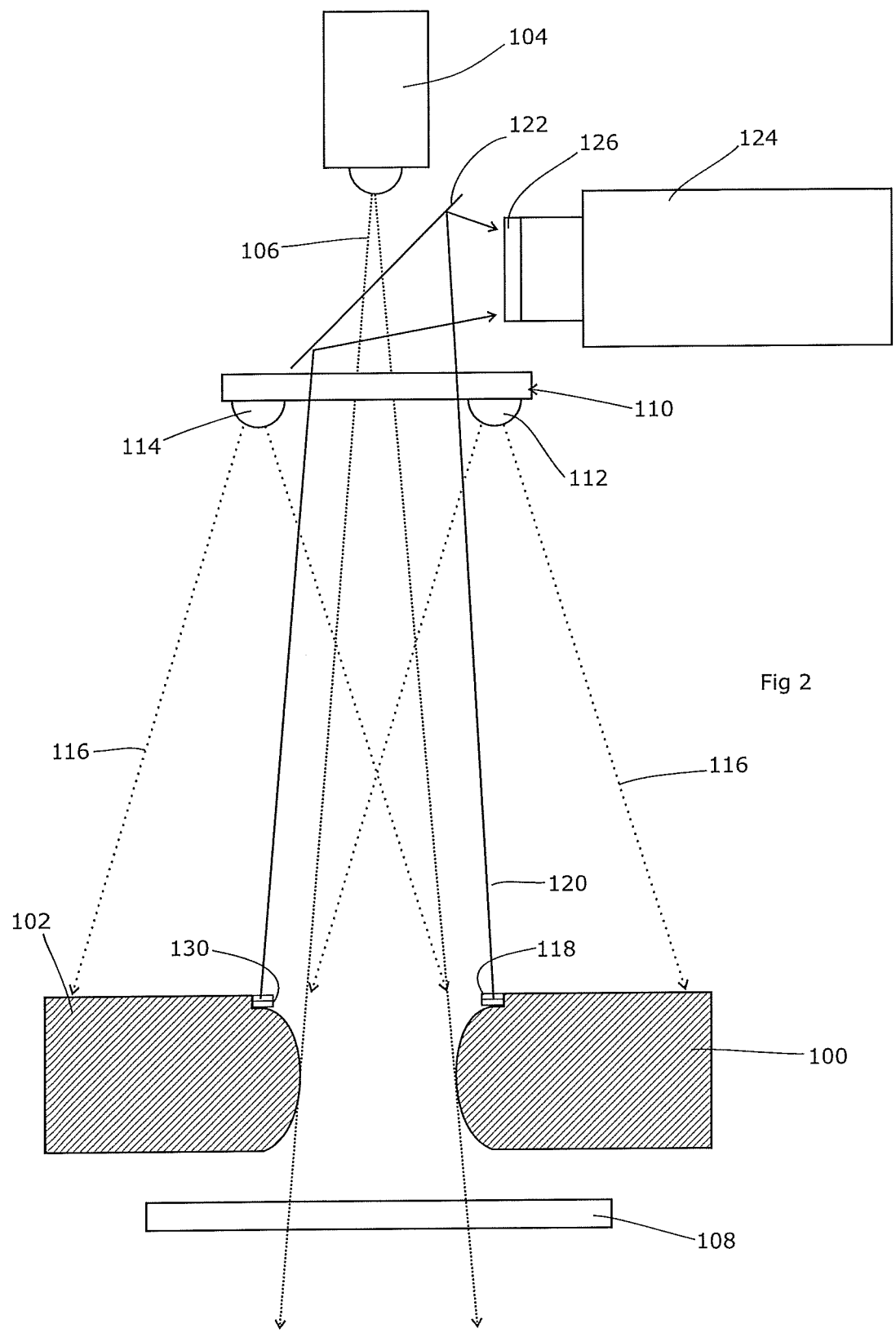
FIG. 2 shows a positional readout arrangement according to the present invention.

FIG. 2 shows an example of the present invention. For simplicity of illustration, the mylar mirror 18 of FIG. 1 has been omitted, so straight paths for some of the optical systems are shown. In practice, this mirror will of course be provided so that sensitive components are removed from the radiation beam and so that components can be placed in convenient locations in the radiation head. The mirrors 16, 24 of FIG. 1 are no longer needed, which leads to a simpler, cheaper and potentially more accurate solution.

Thus, the MLC leaves 100, 102 are illuminated by two difference sources. The first is a green field light projector 104 which emits a beam of green light 106 that covers the entire field, in the form of a point source to allow sharp leaf definition. This light is collimated by the leaves 100, 102 (and any other collimators that may be present) and is allowed out of the head by a green pass mylar screen 108. This light therefore falls onto the treatment table or a patient thereon and allows the operation of the multi-leaf collimator to be verified by an operator.

The second light source is a 410 nm monochromatic source 110, in the form of a diffuse source to provide good machine vision characteristics. In this example, it comprises an array of 410 nm light-emitting diodes 112, 114 which provide a diffuse high intensity light source 116. This light is blocked by the green pass filter 108 and therefore does not fall on the treatment table or patient; as a result it does not confuse the shape of the projected light field and the source therefore does not need to be optically co-located with the radiation source. It can therefore be disposed so as to permit a bright and even illumination of the leaves 100, 102.

Each leaf has at least one ruby marker 118. When illuminated with certain wavelengths of light, Ruby crystals will fluoresce in the dark red\near infra red band—nominally 695 nm. There are a number of so-called "pump" wavelengths which can be used to stimulate this behaviour, specifically 525 nm in the green band and 410 nm in the violet/near ultra violet band.

Thus, the ruby markers 118 will be illuminated by the 410 nm monochromatic source 110, and also by the green field light projector 104 which, at 530 nm or so, may be sufficiently close to the 525 nm excitation wavelength of the ruby material. This will cause the ruby to fluoresce, emitting light in a variety of directions including upwards at 120 and onto a dichroic beamsplitter 122 which diverts a proportion of the light to a camera 124 protected by an infra-red pass filter 126. This IR pass filter 126 will limit the light incident on the camera 124 to that emitted by the fluorescent ruby markers 118, provided that there are no other sources of light at this wavelength in the radiation head.

Fluorescence can be increased by coating the rear surface of the ruby marker with a mirror. The mirror will reflect transmitted light back through the ruby, causing it to fluoresce more.

A particular advantage of this invention is the elimination of reflectors. In the confined and harsh environment of an MLC head, these impose limitations on the performance and longevity of an optical sensing system. Accumulation of dust and dirt requires the markers to be cleaned regularly to maintain correct function. However, regular cleaning can itself degrade the optical performance of the reflectors, while operating conditions can reduce the effectiveness of the adhesive that holds them in place leading to the loss of reflectors.

Also, the use of retro-reflectors imposes further restrictions on the positioning of the light source and camera. In confined spaces the problems caused by this restriction can be considerable. As noted above, the present invention avoids such limitations.

Using a fluorescing marker such as ruby can help overcome these problems. Firstly, ruby is a member of the corundum family and is therefore very hard and easily able to withstand heavy industrial environments. Regular cleaning will not impact the performance of the markers. Secondly, the use of one excitation wavelength but the detection of another allows extraneous noise to be filtered out of the system.

Thirdly, the position of the light source and camera can now be independent of each other, and (for the MLC) the patient illumination and machine vision illumination are now also independent of each other.

So, by illuminating the leaves marked with ruby reflectors with a 410 nm or 525 nm rich light source the ruby markers will radiate red light which may be extracted from the background illumination by utilising a near infra red filter on a video camera. In addition, by filtering external light exiting the head and entering the head, the effect of external lighting effects may be minimised.

The leaves may be marked utilising ruby bearings. Such bearings are readily available commercially and have extremely good dimensional accuracy. This dimensional accuracy, consistency and stability allows the bearings to be mounted accurately by counter sinking or counter boring a hole smaller than the size of the bearing. The tolerance of mounting is therefore potentially the tolerance of the counter bore machining process, which compares favourably to reflectors attached via adhesive.

The system configuration is similar to our original optical system, albeit with several major differences:

1) The retro reflective material would be replaced with the ruby marker, placed using an accurate counter bore.

2) The light projector would be modified to provide two light sources; a 525-530 nm source for patient setup, and a 410 nm source to stimulate fluorescence in the ruby markers. This light source may also be supplemented with a red stop optical filter to remove contamination in the band being sensed, i.e. >600 nm.

3) The camera would be fitted with an infra red pass filter which ideally passes the 695 nm light produced by the fluorescence. This may be further optimised by the use of a band pass filter centred on 695 nm.

4) The external Mylar screen is optically band pass filtered to allow only the wavelength of light through that is being used for patient illumination. This should ideally pass no light over 600 nm, for maximum signal to noise ratio.

Potential advantages include an increase in leaf positioning accuracy, an increase in reflector life (in that the marker should be easier to clean and maintain), a decrease in assembly time due to the easier and more precise placement of the reflector, an increased tolerance of internal stray reflections since the light being sensed is a different wavelength to the illumination, and an increased tolerance to external light interference. Further, should it prove necessary to replace a marker, it might be feasible to do so with no recalibration due to the precise mounting method of the marker.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

What is claimed is:

1. A radiotherapeutic apparatus comprising:
   a source of therapeutic radiation, for generating a beam of therapeutic radiation;
   a first light source, for generating a beam of optical light;
   a multi-leaf collimator comprising a plurality of leaves operative to collimate the beam of therapeutic radiation and the beam of optical light, at least one leaf of the plurality of leaves having a fluorescent marker;
   a second light source, generating diffuse, substantially monochromatic light having a first wavelength for stimulating fluorescence in the fluorescent marker; and
   a camera arranged to view the fluorescent markers.

2. The radiotherapeutic apparatus according to claim 1, further comprising a filter arranged over an output of the multi-leaf collimator, for filtering out light having the first wavelength.

3. The radiotherapeutic apparatus according to claim 1, wherein the first light source is substantially monochromatic such that the beam of optical light has a second wavelength that is different from the first wavelength.

4. The radiotherapeutic apparatus according to claim 3, further comprising a filter arranged over an output of the multi-leaf collimator, for filtering out light having the first wavelength and passing light having the second wavelength.

5. The radiotherapeutic apparatus according to claim 4, wherein the filter is a band-pass filter having a pass band centred on the second wavelength.

6. The radiotherapeutic apparatus according to claim 1, wherein the first light source is optically co-located with the source of therapeutic radiation.

7. The radiotherapeutic apparatus according to claim 1, wherein the first light source is a point source.

8. The radiotherapeutic apparatus according to claim 1, wherein the camera is configured to image radiation at a wavelength of fluorescence of the fluorescent marker.

9. The radiotherapeutic apparatus according to claim 1, wherein the first light source is substantially monochromatic such that the beam of optical light has a second wavelength that is different from the first wavelength, and wherein a wavelength of fluorescence of the fluorescent marker is longer than the first and second wavelengths.

10. The radiotherapeutic apparatus according to claim 1, wherein the camera comprises a filter arranged to substantially prevent light of the first wavelength from entering the camera.

11. The radiotherapeutic apparatus according to claim 1, wherein the beam of optical light comprises substantially no light at the first wavelength.

12. The radiotherapeutic apparatus according to claim 1, wherein substantially all the plurality of leaves have a fluorescent marker.

13. The radiotherapeutic apparatus according to claim 1, wherein at least a first leaf of the plurality of leaves has a plurality of markers.

14. The radiotherapeutic apparatus according to claim 13, wherein a second leaf of the plurality of leaves has a plurality of markers, the second leaf carrying the markers in a configuration that is different to the first leaf.

15. The radiotherapeutic apparatus according to claim 1, wherein the leaves are mounted on a frame, and the frame has at least one fluorescent marker.

16. The radiotherapeutic apparatus according to claim 15, wherein the frame has a plurality of fluorescent markers which collectively indicate a maximum field of irradiation of the multi-leaf collimator.

17. The radiotherapeutic apparatus according to claim 1, wherein the fluorescent marker comprises ruby.

18. The radiotherapeutic apparatus according to claim 1, wherein the fluorescent marker is spherical.

19. The radiotherapeutic apparatus according to claim 1, wherein the fluorescent marker is cylindrical.

* * * * *